United States Patent [19]

Hakomori

[11] Patent Number: 4,904,596
[45] Date of Patent: Feb. 27, 1990

[54] HYBRIDOMA ANTIBODY (FH6) DEFINING A HUMAN CANCER-ASSOCIATED DIFUCOGANGLIOSIDE

[75] Inventor: Sen-itiroh Hakomori, Mercer Island, Wash.

[73] Assignee: Fred Hutchinson Cancer Research Center, Seattle, Wash.

[21] Appl. No.: 763,545

[22] Filed: Aug. 7, 1985

[51] Int. Cl.$^4$ .................. C12N 5/00; C12P 21/00; A61K 39/395; G01N 33/54
[52] U.S. Cl. .................. 435/240.27; 435/948; 435/70.21; 436/548; 935/104; 935/110; 530/387
[58] Field of Search .................. 435/68, 172.2, 240.27, 435/948; 935/104, 107, 110; 424/85; 530/387; 436/548

[56] References Cited

U.S. PATENT DOCUMENTS 4,444,744  4/1984  Goldenberg .................. 436/813
4,471,057  9/1984  Koprowski et al. .................. 436/531

OTHER PUBLICATIONS

Fukushi et al., Cancer Research 45, pp. 3711–3777 (1985).
Magnani et al., Journal of Biological Chemistry 257 (23) pp. 14365–14369 (1982).
Vitetta et al., Science 219, pp. 644–650 (1983).
J. Biol. Chem. 259(16):10511–10517, issue of Aug. 25, 1984.
Biochem. Biophys. Res. Comm. 113(3):791–798, 1983.
J. Biol. Chem. 259(7):4681–4685, 1984.
Cancer Research 44:5279–5285, 1984.
Cancer Research 45:435–437, 1985.

Primary Examiner—John Edward Tarcza

Attorney, Agent, or Firm—Christensen, O'Connor, Johnson & Kindness

[57] ABSTRACT

A hybridoma cell line (ATCC No. HB 8873) secreting a monoclonal IgM antibody (FH6) directed to a fucoganglioside, 6B, which accumulates in human colonic adenocarcinoma but is absent in normal colonic mucosa. The structure of the 6B ganglioside to which the antibody FH6 is directed is as follows:

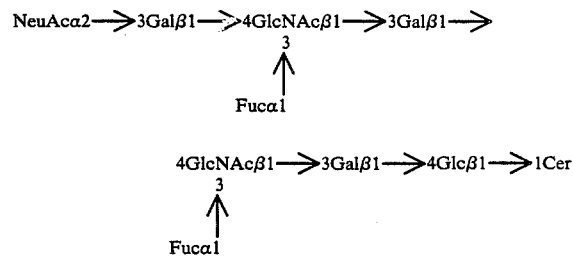

The hybridoma secreting the antibody FH6 was selected by reactivity of the FH6 antibody with the 6B ganglioside (VI$^3$NeuAcV$^3$III$^3$Fuc$_2$nLc$_6$) and lack of reactivity with other glycolipids, including glycolipids having closely related structures, such as sialosyllactoneotetraosylceramide (IV$^3$NeuAcnLc$_4$), sialosyllactofucopentaosy(III)ceramide (IV$^3$NeuAcIII$^3$FucnLc$_4$), sialosyllactofucopentaosy(II)ceramide (sialosyl-Le$^a$ glycolipid; IV$^3$NeuAcIII$^4$FucLc$_4$), and 6C fucoganglioside (sialosyl 2→6 fucoganglioside; VI$^6$NeuAcIII$^3$-FucnLc$_6$). The antibody FH6 is highly reactive with a large variety of human cancer cells, including colonic, lung, and breast cancer, but does not react with most normal adult cels (except, notably, granulocytes). The antibody FH6 is of practical value in diagnostic tests and in monitoring and implementing various cancer treatments.

13 Claims, 5 Drawing Sheets

HYBRIDOMA ANTIBODY (FH6) DEFINING A HUMAN CANCER-ASSOCIATED DIFUCOGANGLIOSIDE

This invention was made partly with Government support under Grants CA20026 and GM23100 from the National Institutes of Health. The Government has certain rights in this invention.

TECHNICAL FIELD

This invention relates to hybridoma cell lines that produce monoclonal antibodies useful for the detection and treatment of human cancers.

BACKGROUND OF THE INVENTION

Dramatic changes in chemical composition, metabolism, and organization of cell-surface glycosphingolipids characterize a common membrane phenotype associated with oncogenic transformation. Recent studies with monoclonal antibodies directed to various human cancers have revealed unusual accumulations of certain glycolipids in human cancer, such as $GD_3$ ganglioside in human melanoma, $Gb_3$ in Burkitt lymphoma, sialosyl-$Le^a$ ganglioside in colorectal, gastric, and pancreatic cancer, and 6C fucoganglioside ($VI^6FucIII^3$-$NeuAcnLc_6$) in colorectal and hepatic cancer. For a review, see Hakamori, S., et al., *J.Natl.Cancer Inst.* 71: 231–251, 1983. More recently, accumulation of glycolipids with di- or trifucosylated type 2 chain has been found in a large variety of human cancers (*J.Biol.Chem.* 259: 4672–4680, 1984), and monoclonal antibodies that can distinguish di- and trifucosylated type 2 chain from monofucosylated type 2 chain have been established (*J.Biol.Chem.* 259: 4681–4685, 1984). One of the antibodies, FH4, specifically reacts with the antigen having difucosylated type 2 chain, which is common in a variety of gastrointestinal and colorectal adenocarcinomas, but is restricted to a few types of cells in normal human gastrointestinal and urogenital epithelial tissues. Other studies of the gangliosides of human adenocarcinoma have shown an accumulation of a large quantity of sialosyl 2→6 lactoneotetraosylceramide (*J.Biol. Chem.* 258: 11819–11822, 1983) and other more complex novel fucogangliosides, termed gangliosides 6B and 6C (*Biochem.Biophys.Res.Commun.* 113: 791–798, 1983). It would be advantageous to isolate and identify the 6B ganglioside and to raise a hybridoma antibody defining this structure and establish its specificity and reactivity in normal and transformed tissue.

SUMMARY OF THE INVENTION

This invention provides a hybridoma cell line (ATCC No. HB 8873) secreting a monoclonal IgM antibody (FH6) directed to a fucoganglioside, 6B, which accumulates in human colonic adenocarcinoma but is absent in normal colonic mucosa. The structure of the 6B ganglioside to which the antibody FHB≠is directed is as follows:

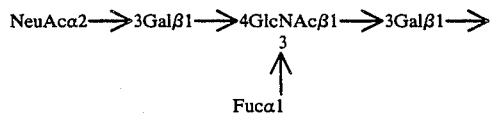

-continued

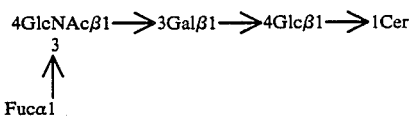

The hybridoma secreting the antibody FH6 was selected by reactivity of the FH6 antibody with the 6B ganglioside ($VI^3NeuAcV^3III^3Fuc_2nLc_6$) and lack of reactivity with other glycolipids, including glycolipids having closely related structures, such as sialosyllactoneotetraosylceramide ($IV^3$ $NeuAcnLc_4$), sialosyllactofucopentaosy(III)ceramide ($IV^3NeuAcIII^3FucnLc_4$), sialosyllactofucopentaosy(II)ceramide (sialosyl-$Le^a$ glycolipid; $IV^3NeuAcIII^4FucLc_4$), and 6C fucoganglioside (sialoyl 2→6 fucoganglioside; $VI^6NeuAcIII^3$-$FucnLc_6$). The antibody FH6 is highly reactive with a large variety of human cancer cells, including colonic, lung, and breast cancer, but does not react with most normal adult cells (except, notably, granulocytes). Since the 6B ganglioside is a useful marker of cancer antigens, the antibody FH6 is of practical value in diagnostic tests and in monitoring and implementing various cancer treatments.

DESCRIPTION OF THE PREFERRED EMBODIMENT

Figure 1:
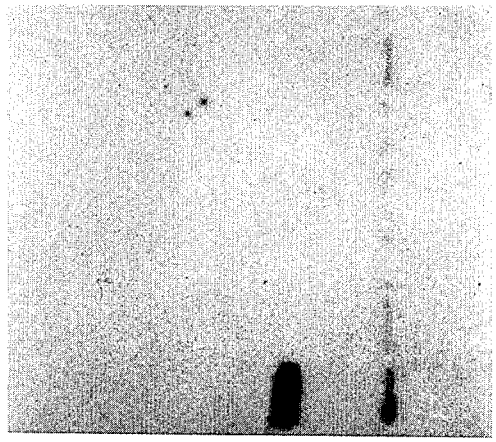
FIG. 1 is a replicate pair of HPTLC patterns (a & b) of purified fucogangliosides, wherein one of the patterns (b) has been immunostained by the monoclonal antibody FH6, as described in Example 3.
Figure 1:
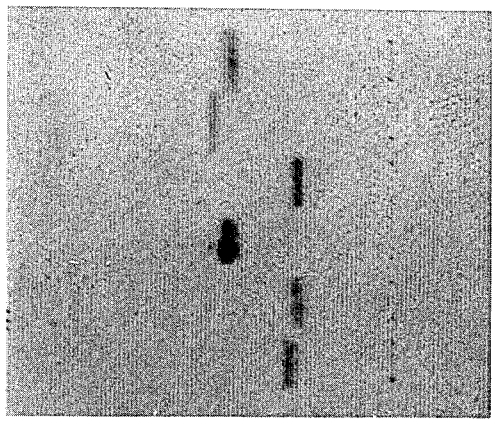

Glycolipids are designated and abbreviated herein according to the recommendations of the Nomenclature Committee of the International Union of Pure and Applied Chemistry, as stated in *Lipids* 12: 455–463, 1977.

This invention provides a hybridoma cell line capable of producing a monoclonal antibody capable of specifically binding with the 6B fucoganglioside, $VI^3$-$NeuAcV^3III^3Fuc_2nLc_6$. Hybridoma cell line ATCC No. HB 8873 expresses an IgM monoclonal antibody (FH6) that specifically reacts with the fucogangliosides $VI^3NeuAcV^3III^3Fuc_2nLc_6$ and $VI^3NeuAcV^3FucnLc_6$, but that does not specifically react with $IV^3NeuAcIII^3$-$FucnLc_4$, $IV^3NeuAcIII^4FucLc_4$, $VI^6NeuAcIII^3$-$FucnLc_6$, $V^3III^3Fuc_2nLc_6$, $IV^3NeuAcnLc_4$, or $VI^3$-$NeuAcnLc_6$. See TABLE I and Examples 3 and 4.

TABLE I

Structures of novel fucogangliosides and their reactivity with the monoclonal antibody FH6

| | Structure | Reactivity |
|---|---|---|
| 1. 6B ganglioside (studied in this paper) | $Gal\beta1 \xrightarrow{3} 4GlcNAc\beta1 \xrightarrow{3} 3Gal\beta1 \xrightarrow{} 4GlcNAc\beta1 \xrightarrow{3} 4Glc\beta1 \rightarrow 1Cer$<br>   ↑               ↑<br>NeuAcα2      Fucα1 | ++ |
| 2. IV³NeuAcIII³FucnLc₄ (Rauvala's ganglioside) | $Gal\beta1 \xrightarrow{} 4GlcNAc\beta1 \xrightarrow{3} 3Gal\beta1 \xrightarrow{} 4Glc\beta1 \rightarrow 1Cer$<br>   ↑3        ↑<br>NeuAcα2   Fucα1 | – |
| 3. IV³NeuAcIII⁴FucnLc₄ (sialosyl-Leᵃ) | $Gal\beta1 \xrightarrow{} 3GlcNAc\beta1 \xrightarrow{} 4Glc\beta1 \rightarrow 1Cer$<br>   ↑3      ↑4<br>NeuAcα2  Fucα1 | – |
| 4. 6C fucoganglioside (VI⁶NeuAcIII³FucnLc₆) | $Gal\beta1 \xrightarrow{} 4GlcNAc\beta1 \xrightarrow{3} 3Gal\beta1 \xrightarrow{} 4GlcNAc\beta1 \xrightarrow{} 4Glc\beta1 \rightarrow 1Cer$<br>   ↑6                       ↑<br>NeuAcα2               Fucα1 | – |
| 5. Band 4 glycolipid (asialo 6B; V³III³Fuc₂nLc₆) (10) | $Gal\beta1 \xrightarrow{} 4GlcNAc\beta1 \xrightarrow{3} 3Gal\beta1 \xrightarrow{} 4GlcNAc\beta1 \xrightarrow{} 4Glc\beta1 \rightarrow 1Cer$<br>   ↑                      ↑<br>Fucα1              Fucα1 | – |

The antibody FH6 is highly reactive with a large variety of human cancer cells, including colonic, lung, and breast cancer, but is essentially unreactive with most normal adult cells (except, notably, granulocytes). Since the antigen defined by FH6 is a useful marker of cancer antigens, the antibody FH6 is of practical value in diagnostic tests and in monitoring and implementing various cancer treatments. For example, the antibody FH6 can be coupled to a radionuclide and introduced into the body of a mammal to image cancer cell location and/or implant radiotherapy. The antibody FH6 can be similarly coupled to an antitumor drug for cancer therapy.

The monoclonal antibody FH6 can also be coupled to a detectable marker for immunohistological detection of cells that express the 6B fucoganglioside. The detectable marker can be selected from among fluorophores, enzymes, chromophores, coenzymes, chemiluminescent materials, enzyme inhibitors, and radionuclides that are well known in the art. Cells such as from a biopsy can then be contacted with the FH6-marker conjugate, and any detectable marker that becomes sequestered on the cells can be detected by standard techniques after unreacted antibody is washed from the cells. Normal human granulocytes can be detected in the same manner using the antibody FH6. Tumor-associated antigen in blood serum can also be detected in blood serum using standard immunoassays but employing the antibody FH6.

The following Examples are presented to illustrate the advantages of the present invention and to assist one of ordinary skill in making and using the same. The following Examples are not intended in any way to otherwise limit the scope of the disclosure or the protection granted by Letters Patent hereon.

EXAMPLE 1

Isolation and characterization of the 6B ganglioside

The 6B ganglioside was isolated and characterized as described in $J.Biol.Chem.$ 259(16): 10511–10517, 1984, hereby incorporated by reference. Briefly summarized here, monosialogangliosides were extracted from human colonic cancer tissue, in particular, human colonic adenocarcinomas FT75-620 and FT75-845 metastatic to liver (Tumor Procurement Program, National Institute of Health). The monosialogangliosides were purified by two high-performance liquid chromatography (HPLC) steps to separate a fraction containing the 6B and 6C but no other gangliosides. That fraction was purified by preparative high-performance thin-layer chromatography (HPTLC) to yield a pure preparation of the 6B ganglioside. The structure of the homogeneous 6B ganglioside was determined by methylation analysis, direct probe mass spectrometry of permethylated compounds, hydrolysis with sialidase in the absence of detergent, and solid-phase radioimmunoassay of the desialylated core glycolipid by two monoclonal antibodies, FH3 and FH4. Fatty acid composition was analyzed by chemical ionization/mass spectrophotometry.

The 6B ganglioside was identified as a monosialo derivative of difucosyllactonorhexaosylceramide ($III^3V^3Fuc_2nLc_6$): sialosyl 2→3 linked to the terminal Gal residue of $III^3V^3Fuc_2nLc_6$, or $VI^3NeuAcV^3III^3Fuc_2nLc_6$, as shown in TABLE I, structure 1. The fatty acid composition of the 6B ganglioside was characterized by a majority of short-chain nonhydroxylated fatty acids.

EXAMPLE 2

Preparation of the monoclonal antibody

A modification ($J.Exp.Med.$ 150: 1008–1019, 1979) of the procedure originally described by Köhler and Milstein ($Nature (Lond.)$) 256: 495–497, 1975) was followed by establishing hybridomas producing monoclonal antibodies. The 6B fucoganglioside, isolated and characterized as in Example 1, was adsorbed to $Salmonella\ minnesota$ ($J.Exp.Med.$ 150: 1008–1019, 1979; $Eur.J.Biochem.$ 24: 116–122, 1971) and was used as the immunogen. An ethanol solution (50 $\mu$l) containing 20 $\mu$g of purified 6B ganglioside ($VI^3NeuAcV^3III^3Fuc_2nLc_6$) was mixed with 800 $\mu$l; of phosphate-buffered saline (pH 7.4). The solution was mixed with 259 $\mu$g of acid-treated $S.\ minnesota$ ($Biochemistry$ 14: 2725–2733, 1975) suspended in 250 $\mu$l of phosphate-buffered solution. The whole mixture was thoroughly mixed at 40° C. The suspension containing 5 $\mu$g of the glycolipid was intravenously injected on the first day into Balb/c mice. Subsequently, an aliquot containing 2 $\mu$g of the glycolipid was injected three times on every fourth day.

Fusion of the host spleen cells with commercially available mouse myeloma SP-2 cells was performed on the third day after the last injection. Hybridomas were cloned on 96-well plates (Dynatech Immunolon plate, Dynatech Laboratories, Alexandria, VA) coated with purified $VI^3NeuAcV^3III^3Fuc_2nLc_6$ glycolipid (10 ng/well), cholesterol (30 ng/well), and lecithin (50 ng/well). Cloning was performed repeatedly.

The hybridoma secreting the FH6 antibody was selected from a number of clones, as described in Examples 3 and 4. Ascites of the hybridoma producing FH6 had a titer of 1:25,000.

EXAMPLE 3

Determination of the antibody specificity

The hybridoma secreting the monoclonal antibody FH6 was selected by reactivity with the 6B ganglioside and lack of crossreactivity with other fucogangliosides having closely related structures.

TABLE I shows the structures of several fucogangliosides used in this assay. Structure 1 is the 6B ganglioside as described above. Structure 2 is sialosyllactofucopentaosyl(III)ceramide ($IV^3NeuAcIII^3FucnLc_4$), prepared from human kidney as described in $J.Biol.Chem.$ 251: 7517–7520, 1976. Structure 3 is sialosyllactofucopentaosyl(II)ceramide (sialosyl Le$^a$; $IV^3NeuAcIII^4FucLc_4$), prepared from human colonic cancer tissue (FT 620) as described in: $J.Biol.Chem.$ 257: 14365–14369, 1982; $Biochem.Biophys.Res.Commun.$ 110: 383–391, 1983.

Structure 4 is the 6C fucoganglioside ($VI^6NeuAcIII^3FucnLc_6$), prepared from human colonic cancer tissue and separated from the 6B ganglioside as described in: $J.Biol.Chem.$ 259: 10511–10517, 1984; $Biochem.Biophys.Res.Commun.$ 113: 791–798, 1983. Structure 5 is the asialo core of the 6B ganglioside ($V^3III^3Fuc_2nLc_6$); $J.Biol.Chem.$ 259: 4672–4680, 1984. Other fucogangliosides used in this assay include the following: difucosyllactonorhexasylceramide ($III^3V^3Fuc_2nLc_6$), prepared from human cancer as described in $J.Biol.Chem.$ 259: 4672–4680; 1984; and sialosyl 2→3 lactoneotetraosylceramide (sialosylparagloboside; $IV^3NeuAcnLc_4$), prepared from human erythrocytes as described in $J.Biol.Chem.$ 254: 8223–8229, 1979.

The aforesaid glycolipids separated on HPTLC were immunostained according to a modified procedure (*J.Biol.Chem.* 257: 14865-14874, 1982) of Magnani et al. (*Anal.Biochem.* 109: 399-402, 1980). A mini-HPTLC plate was used in order to minimize the amounts of glycolipid and antibody. A Baker HPTLC plate (J. T. Baker Chemical Co.) was cut into 5×6 cm pieces by a glass cutter. Glycolipid samples (about 0.2-0.3 μg) were applied on duplicate plates by needle syringe (Hamilton Co., Reno, NV) on a baseline within 3-4 mm. Glycolipid bands were developed in chloroform/methanol/water (50:40:10) containing 0.02% $CaCl_2$. Spots on the control chromatograms (FIG. 1a) were detected by 0.2% orcinol in 2N sulfuric acid. The duplicate plates (FIG. 1b) were immunostained with undiluted supernatant of FH6 culture.

Representative results are shown in FIG. 1. The HPTLC pattern of purified fucogangliosides shown in FIG. 1a are as follows: lane 1, 6B ganglioside (TABLE I, structure 1); lane 2, 6C ganglioside (TABLE I, structure 4); lane 3, $IV^3NeuAcIII^3FucnLc_4$ (TABLE I, structures 2); lane 4, $III^3V^3Fuc_2nLc_6$; lane 5, $IV^3$-$NeuAcnLc_4$; lane 6, sialosyl-Le$^a$ (TABLE I, structure 3). The duplicate plate that was immunostained with undiluted supernatant of FH6 culture is shown in FIG. 1b. The antibody FH6 reacted only with the 6B ganglioside (lane A).

Later studies indicated that the monoclonal antibody FH6 also reacted with sialylmonofucosyllactonorhexaosylceramide ($VI^3NeAcV^3FucnLc_6$, 7B ganglioside; *Biochem.Biophys.Res.Commun.* 113: 791-798, 1983). The reactivity of the antibody FH6 with the 7B ganglioside was on the order of half the reactivity it exhibited with 6B ganglioside. These later studies also confirmed that none of the other stated glycolipids with related structures are reactive with the antibody FH6.

EXAMPLE 4

Reactivity of various fucogangliosides with the monoclonal antibody FH6

The specificity of the monoclonal antibody FH6 was also determined by solid-phase radioimmunoassay with antibody dilution as well as antigen dilution. Solid-phase radioimmunoassay was performed on vinyl strips (Costart Laboratories, Cambridge, MA) according to the procedure described in *Cancer Res.* 43: 4997-5005, 1983. Reactivities with antibody dilution (FIG. 2A) were determined with 10 ng of glycolipid, 50 ng of lecithin, and 30 ng of cholesterol coated per well; the original antibody was a twice-diluted culture supernatant of the FH6 hybridoma. In determining reactivities with antigen dilution (FIG. 2B), the original concentration of glycolipid antigen was 125 ng/well, double-diluted over 12 wells; the antibody concentration applied to each well was 1:30 diluted culture supernatant of the FH6 hybridoma.

Figure 2:
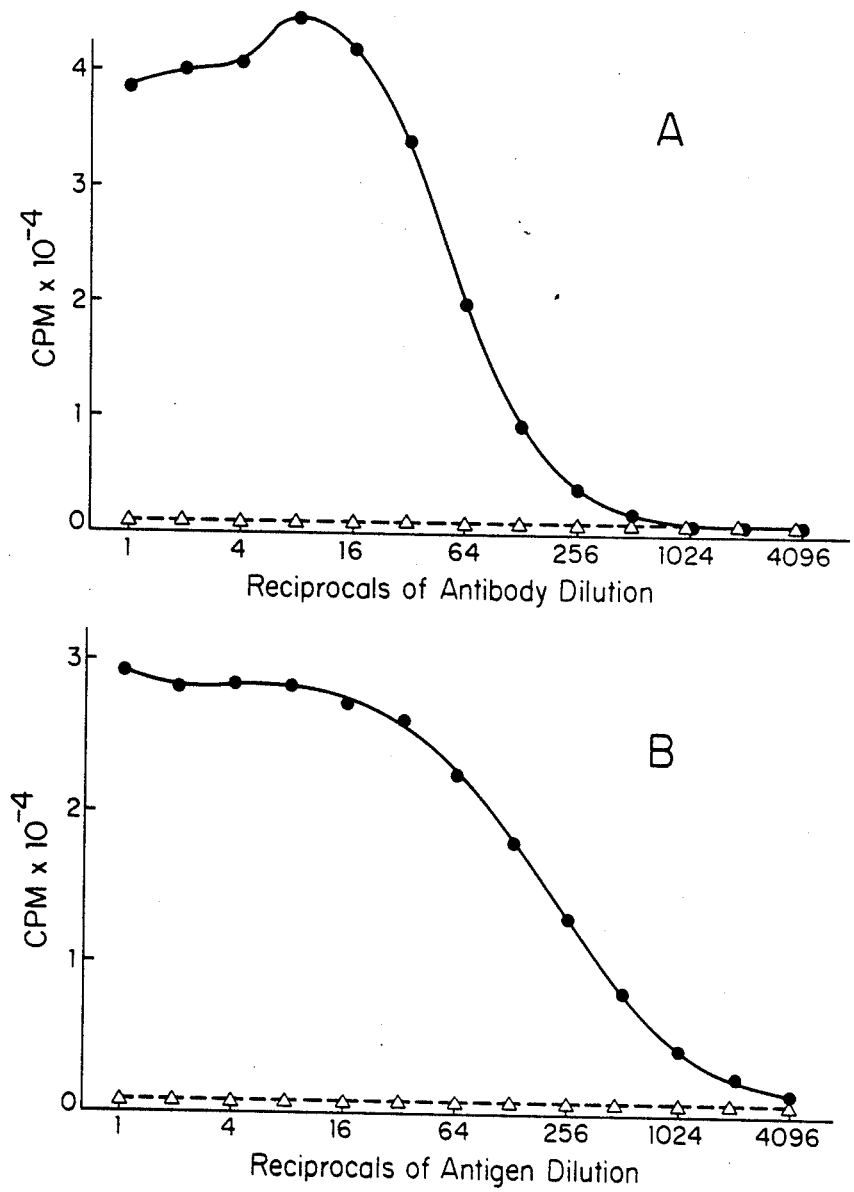
FIG. 2 is two graphs (A & B) demonstrating the reactivity of various fucogangliosides with the monoclonal antibody FH6, wherein reactivities with both antibody dilution (A) and antigen dilution (B) are shown, as described in Example 4.

Referring to the representative results shown in FIGS. 2A and 2B, the positive reactivity indicated by the solid circles represents the 6B ganglioside. In contrast, the negative reactivity indicated by the open triangles was observed for the following gangliosides: $IV^3$-$NeuAcIII^3FucnLc_4$ (TABLE I, structure 2); sialosyl 2→3 lactoneotetraosylceramide ($IV^3NeuAcnLc_4$); the 6C ganglioside (TABLE I, structure 4); and sialosyl 2→3 lactonorhexaosylceramide ($VI^3NeuAcnLc_6$) prepared from human cancer tissue as described in *Biochem. Biophys.Res.Commun.* 113: 791-798, 1983. Data for the negative reactivity with asialo core of 6B is not shown.

EXAMPLE 5

Determination of immunoglobulin subclass

The immunoglobulin subclass of the antibody FH6 was determined with subclass-specific antibodies purchased from Cappel Laboratories (Cochranville, PA). FH6 was determined to be an IgM antibody.

EXAMPLE 6

Reactive of various human tumor cell lines with the monoclonal antibody FH6

The reactivity of the FH6 antibody with a number of human tumor cell lines was studied in comparison with that of the FH4 antibody. The FH4 antibody recognizes the core structure difucosylated lactonorhexaosylceramide ($III^3V^3Fuc_2nLc_6$), as described in: *J.Biol.Chem.* 259(7): 4681-4685, 1984; *J.Exp.Med.* 159: 506-520, 1984.

The human tumor cell lines indicated on the ordinate of FIG. 3 were as follows: Gastric cancer cell lines, MKN series; lung cancer cell lines, QG and PC series; epidermal tumor cells GT-4; ovarial adenocarcinoma SK-OV3; B cell lines, Prentice and Kasner; human fibroblasts, Crowford and WI-38; monocytic leukemia cell line THP-1; human fibroblasts L-5; human teratocarcinoma 2102; and human cervical carcinoma HeLa. The origin of these cell lines has been reported in various papers as described in *J.Biol.Chem.* 259: 4681-4685, 1984. Cells were fixed on polysine-coated Linbro plates (Flow Laboratories, McLean, VA) by treating with glutaraldehyde, and antibody binding was determined as described in *J.Biol.Chem.* 259(7): 4685-4685, 1984.

Figure 3:
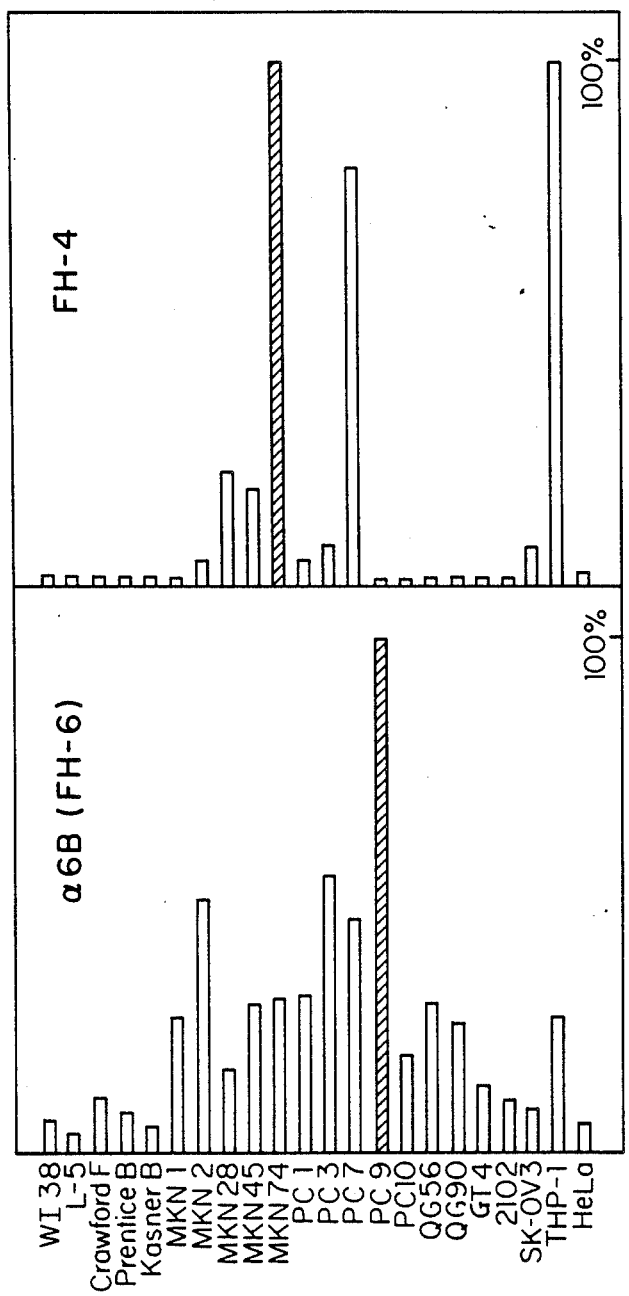
FIG. 3 is a pair of bar graphs that compare the reactivities of antibodies FH6 (left panel) and FH4 (right panel) with various human tumor cell lines, as described in Example 6.

Referring to FIG. 3, the reactivities of the FH6 antibody (left panel) are expressed as the percent of the highest reactivity expressed by lung cancer cell line PC-9 (shaded bar). For comparison, the reactivities of the FH4 antibody are shown in the right panel, expressed as the percent of the highest reactivity expressed by MKN 74. The antibody FH6 demonstrated a high reactivity with various cell lines, particularly lung cancer cell lines, which were negative with FH4.

Discussion

The 6B ganglioside was clearly identified as a monosialo derivative of difucosyllactonorhexaosylceramide ($III^3V^3Fuc_2nLc_6$) a shown in TABLE I. The accumulation of this unique structure in human adenocarcinomas and its absence in normal colonic mucosa (see below) is compatible with previous observation that band 4 glycolipid, which has the same core carbohydrate structure as this ganglioside, accumulates in various human adenocarcinomas. *J.Biol.Chem.* 259: 4672-4680, 1984; *J.Biol.Chem.* 259: 4681-4685, 1984.

Although the asialo core carbohydrate of the 6B ganglioside is identical to the difucosyllactonorhexaosyl in the band 4 glycolipid, the fatty acid profile of the 6B ganglioside (*J.Biol.Chem.* 259: 10511-10517, 1984) showed an interesting difference from that of the band 4 glycolipid. The major fatty acids in the 6B ganglioside were $C_{16:0}$ (35%) and $C_{16:1}$ (10%), and the 6B ganglioside did not contain any α-hydroxy fatty acids nor any appreciable amounts of long-chain fatty acids. In contrast, "4b," a major subfraction of band 4, had long-chain α-hydroxy fatty acids as the major component ($C_{24:0}$ α-OH (61%), and $C_{24:1}$ α-OH (14%)); "4d," another major subfraction of band 4 glycolipid, had as high as 85% of $C_{16:0}$ α-hydroxy fatty acids. Only "4a" and "4e" had short-chain nonhydroxy fatty acids; both were minor subfractions of band 4 glycolipid. This contrasting profile of fatty acid composition between neutral glycolipids and their sialosyl derivatives may indicate that neutral glycolipids having short-chain nonhydroxy fatty acids are selectively sialylated to become the 6B ganglioside. A similar correlation between the terminal carbohydrate structure and fatty acid profile of ceramide was previously described in gangliosides and neutral Le$^x$ glycolipids of human erythrocyte membranes (J.Biol.Chem. 256: 10967–10972, 1981). The 6B ganglioside migrated by HPTLC faster than its asialo core neutral glycolipid. This relationship is opposite to many gangliosides which migrate more slowly than their asialo core, but is similar to G9 fucoganglioside of human erythrocytes (J.Biol.Chem. 254: 8223–8229, 1979). A striking conformational change induced by desialylation is suggested to explain this unusual HPTLC behavior of 6B and G9 gangliosides. The previously established monoclonal antibody FH4 defines the core structure difucosylated lactonorhexaosylceramide (III$^3$V$^3$Fuc$_2$nLc$_6$). The monoclonal antibody FH6 recognizes the counterpart of the fucoganglioside structure recognized by FH4. The antibody FH6 does not crossreact with the shorter chain glycolipid with the same terminal structure, i.e., sialosyllactofucopentaosyl-(III)ceramide, the antigen isolated and characterized previously from human kidney (J.Biol.Chem. 251: 7517–7520, 1976). The lack of reactivity of sialosyllactofucopentaosyl(III)ceramide with FH6 indicates that FH6 requires a carrier carbohydrate with a longer chain or that the second fucosyl residue alters the conformation of the 6B ganglioside in such a way that the terminal determinant recognized by FH6 is exposed. Such a conformation may be absent in sialosyllactofucopentaosyl(III)ceramide. This disparate reactivity is not surprising because one monoclonal antibody, FH1, does not react with the X determinant having a short carbohydrate chain (lactofucopentaosyl(III)ceramide) but reacts strongly with the same X determinant with a longer carbohydrate chain. J.Biol.Chem. 259: 4681–4685, 1984. Interestingly, reactivities of various tumor cell lines with the antibody FH6 were wider and more intense than those with FH4, as shown in FIG. 3. Particularly, lung cancer cells (PC series and QG series) that did not react with FH4 were strongly reactive with FH6. Some tumor cells are able to synthesize the core structure but are unable to sialylate the terminal galactose, whereas other tumor cell populations are capable of completing the 6B fucoganglioside to which the antibody FH6 is specifically reactive.

Studies indicate that the structure defined by the FH4 antibody is highly expressed in gastrointestinal epithelia of fetuses up to 60–70 days and decline dramatically thereafter on further development of gastrointestinal epithelia. Finally, in adult gastrointestinal epithelia, the antigen expression is mainly limited to specific types of cells in gastric and intestinal epithelia, but the antigen is not expressed in colonic epithelia. The high expression of FH4 in gastrointestinal and colorectal carcinoma clearly indicates that FH4 expression is oncofetal. It is clearly contemplated that the antigen defined by FH6 is also oncofetal. Further extensive studies on the distribution of the two structures defined by FH4 and FH6 in various normal and tumor tissues are reported below. The synthesis of the 6B fucoganglioside may require three types of biochemical reactions: (i) chain elongation of the N-acetyllactosaminyl unit which is performed by alternative glycosylation through galactosyl β1→4 and N-acetylglucosaminyl β1→3 linkage; (ii) α1→3 fucosylation of every GlcNAc residue, probably through a qualitatively altered fucosyltransferase; and, (iii) α2→3 sialylation of terminal galactosyl residues. The first process occurs in normal tissue, although it may be enhanced in cancer tissue. The second process seems to be greatly enhanced in various human cancers. Not all tissues that have a high quality of the FH4-define structure express the fucoganglioside defined by FH6; therefore, the sialylation process of the FH4-defined structure may be greatly enhanced in some malignancies but not others.

EXAMPLE 7

Distribution of the antigen defined by the antibody FH6 in normal adult and fetal tissue as compared with tumor tissues The distribution of the antigen defined by the monoclonal antibody FH6 was determined in normal adult and fetal tissue as compared with tumor tissues.

Materials and Methods

Tissues

Twenty samples of apparently normal regions of adult tissue obtained from surgical operations and 66 samples of various human cancer tissues were obtained from the Departments of Surgery and Pathology, Swedish Hospital Medical Center, Seattle, WA, and Japan Immunoresearch Laboratories, Takasaki, Japan. All these sample were early stages of primary cancer tissue and adjacent normal tissue and were obtained on surgical operation. Tissues were immediately processed for preparation of "frozen sections" or "formalin-fixed paraffin sections" as described below under "Preparation of tissue sections." Fourteen human embryos and fetuses were obtained from the Division of Human Embryology and Teratology, Department of Pediatrics, University of Washington, Seattle, WA. The embryos and fetuses were between 38 and 127 days old and were collected and staged as described in Monitoring Birth Defects and Environment: The problem of surveillance, E. B. Hook, et al., eds., pp. 29–44, Academic Press, N.Y., 1971.

Antibodies and other reagents

The IgM monoclonal antibody FH6 directed to difucosylganglioside 6B was established as described in Example 2. Antibody from either culture supernatant or ascites fluid was precipitated by addition of 2 volumes of saturated ammonium sulfate. The precipitate was solubilized in water and applied on a Sepharose CL6B column. The IgM fraction (Fractions 25 to 35, each fraction 5 ml) was rechromatographed on a CL6B column, dialyzed against PBS (phosphate buffered saline: 140 mM NaCl containing 10 mM sodium phosphate buffer, pH 7.0), and stabilized by addition of 0.1% bovine serum albumin. The final concentration of antibody was adjusted to 100 μg/ml, which was approximately equivalent to a 10-fold dilution of ascites. The secondary antibody (rabbit immunoglobulin directed to mouse immunoglobulin) conjugated with horseradish peroxidase was purchased from Accurate Chemical Co. (Westbury, NY). Vectostain ABC Kit, which includes biotinyl antibody and avidin to increase the sensitivity of immunostaining, was obtained from Vector Laboratories, Inc. (Burlingame, CA).

Preparation of tissue sections

Fresh surgical specimens were embedded in OCT compound (Tissue-Tek Division, Mile Laboratories, Inc., Naperville, IL), frozen in dry ice-acetone, and stored in a Revco freezer at $-80°$ C. until used. Frozen sections (4 to 6 $\mu$m thick) were prepared on a cryostat. Each section was dried on an objective glass for 30 minutes at room temperature, fixed in acetone at 4° C., for 10 min, and washed with PBS at 4° C. Formalin-fixed paraffin sections (6 to 8 $\mu$m thick) were also prepared from phosphate-buffered formalin-fixed, paraffin-embedded tissues according to an established procedure described in Sheehan, D.C., et al., *Theory and Practice of Histotechnology*, Ed. 2, pp. 59-88, The C. V. Mosby Co., St. Louis, 1980. Sections were deparaffinized in xylene for 5 min at 4° C., dehydrated in ethanol, and washed with PBS. Either frozen sections or formalin-paraffin sections were then blocked by incubation with 15% normal rabbit or horse serum in PBS for 2 hours at room temperature, followed by immunostaining as described below.

Immunostaining procedure

After they were blocked with normal rabbit or horse serum, sections were incubated with the primary antibody FH6 (as either nondiluted culture supernatant or 20-fold-diluted ascites) for 18 hours in a moist chamber at 4° C. and washed three times with PBS at 4° C. Each washing took 5 min. The sections were then incubated with peroxidase-conjugated secondary antibody (diluted 1:30) for one hour at room temperature in a moist chamber and washed three times in PBS at 4° C. as above. Bound antibodies were detected by incubating sections in 0.5M Tris-HCl buffer, pH 7.6, containing 0.03% 3,3'-diaminobenzidine (Sigma Chemical Co., St. Louis, MO) and 0.008% hydrogen peroxide. For application of the Vectostain ABC kit, sections were treated with anti-mouse IgM horse antibody containing biotinyl residue followed by avidin-biotinyl horseradish peroxidase; finally, the sections were treated with the benzidine reagent as above. In either case, after 10 min of staining the sections were washed with distilled water, counterstained with hematoxylin, dehydrated on ethanol, washed with xylene, and mounted. Two controls were performed for each staining experiment: (a) sections treated without the primary antibody, and (b) sections treated with normal mouse serum.

Immunostaining of the antigen in frozen sections and in paraffin-embedded sections was compared in view of a possible elimination of glycolipid antigens during preparation of sections from paraffin-embedded specimens. There were no significant differences in immunoreactivity between frozen sections and paraffin sections for both fetal and adult samples.

Results

The results of the staining of normal fetal and adult tissues by the FH6 antibody are summarized in TABLE 2.

TABLE 2

Staining of fetal and adult tissue by FH6 monoclonal antibody

| | Stomach | Colon | Liver | Small intestine | Pancreas | Esophagus | Mammary glands | Lung | Heart | Skin | Brain | Uterine tube | Granulocytes | Lymphocytes | Erythrocytes |
|---|---|---|---|---|---|---|---|---|---|---|---|---|---|---|---|
| Fetal cases | | | | | | | | | | | | | | | |
| 38 days (P)[a] | +[b] | + | | + | + | | | | | | | | | | |
| 40 days (P) | + | | | + | | | | | | | | | | | |
| 40 days (F) | | | | | | | | | | | − | | | | |
| 53 days (P) | + | ++ | | ++ | ++ | | | | | | | | | | |
| 54 days (P) | | | | ++ | | + | | + | | | | | | | |
| 55 days (P) | + | | | + | | | | | + | | − | | | | |
| 57 days (P) | | | | | | | | | | | − | | | | |
| 58 days (P) | + | + | | ± | + | | | + | | | | | | | |
| 59 days (P) | | | | | | | | | + | | − | | | | |
| 72 days (P) | ± | | | ±± | | | | ++ | | | ± | | | | |
| 72 days (F) | | | | | | | | | | | − | | | | |
| 84 days (P) | ± | | | ± | | | | | | | | | | | |
| 110 days (P) | | | | | | | | | | | | | | | |
| 127 days (P) | | | | | | | | | | | | | | | |
| Adult cases | | | | | | | | | | | | | | | |
| | − (3/3)[c] | − (3/3) | − (1/2) | − (1/1) | ND | ND | − (1/1) | − (1/1) | | − (1/1) | ND | − (1/1) | +[d] | −[d] | −[d] |
| (F) | ND | − (6/6) | − (1/1) | | | | − (1/1) | − (3/3) | | − (1/1) | ND | | | | |

Referring to TABLE 2, a diffuse, weak, but obvious, immunostaining of the antigen by the FH6 antibody was observed in the epithelial region of a large variety of tissue sections from human embryos and fetuses at various stages of development. However, no staining was observed in the epithelial or interstitial regions of the normal adult tissues thus far tested, with the exception of the epithelial cells of proximal convoluted tubuli of kidney, which showed a clearly positive staining. In addition, blood cells, granulocytes showed a clearly positive staining. Lymphocytes, monocytes, and erythrocytes were negative. Interestingly, the antibody FH4, which is directed to the asialo core of FH6 antigen, showed very weak or no staining with normal granulocytes (data not shown).

The results of the staining of cancer tissues by the monoclonal antibody FH6 are summarized in TABLE 3.

TABLE 3

Staining of cancer tissues by FH6 monoclonal antibody

| Cancers | Reactivity | | | |
|---|---|---|---|---|
| | ++[a] | + | ± | − |
| Stomach cancer (P)[b] | 1/15[c] | 6/15 | 3/15 | 5/15 |
| adenocarcinoma (F) | ND | ND | ND | ND |
| Colon cancer (P) | 0/5 | 2/5 | 0/5 | 3/5 |
| adenocarcinoma (F) | 0/10 | 0/10 | 3/10 | 7/10 |
| Lung cancer (P) | 0/2 | 0/2 | 1/2 | 1/2 |
| squamous cell (F) carcinoma | 0/4 | 0/4 | 2/4 | 2/4 |
| Breast cancer (P) | 2/4 | 2/4 | 0/4 | 0/4 |
| infiltrating (F) ductal carcinoma | 0/11 | 2/11 | 7/11 | 2/11 |
| Malignant melanoma (P) | ND | ND | ND | ND |
| (F) | 0/1 | 0/1 | 0/1 | 1/1 |
| Ovarian cancer (P) | 0/1 | 0/1 | 0/1 | 1/1 |
| (F) | 0/2 | 0/2 | 1/2 | 1/2 |
| Prostatic cancer (P) | ND | ND | ND | ND |
| adenocarcinoma (F) | 0/1 | 0/1 | 1/1 | 0/1 |
| Renal cancer (P) | 5/20 | 2/20 | 4/20 | 9/20 |
| adenocarcinoma (F) | ND | ND | ND | ND |

[a]++, strong staining; +, clear positive staining; ±, weak staining; −, negative staining.
[b](P), parafin-embedded section; (F), frozen section; ND, not done.
[c]Numerator, case number with the indicated reactivity; denominator, number of cases examined.

Positive staining with FH6 was observed in tissue sections from 44 of 76 cases of stomach, breast, lung, and renal cancers, although the intensity of staining was relatively weak as compared with that of the difucosyl type 2 chain antigen defined by FH4 antibody (data not shown). The highest incidence of positive staining (86%) by the antibody FH6 was observed in breast cancer (infiltrating ductal carcinoma).

Figure 4:
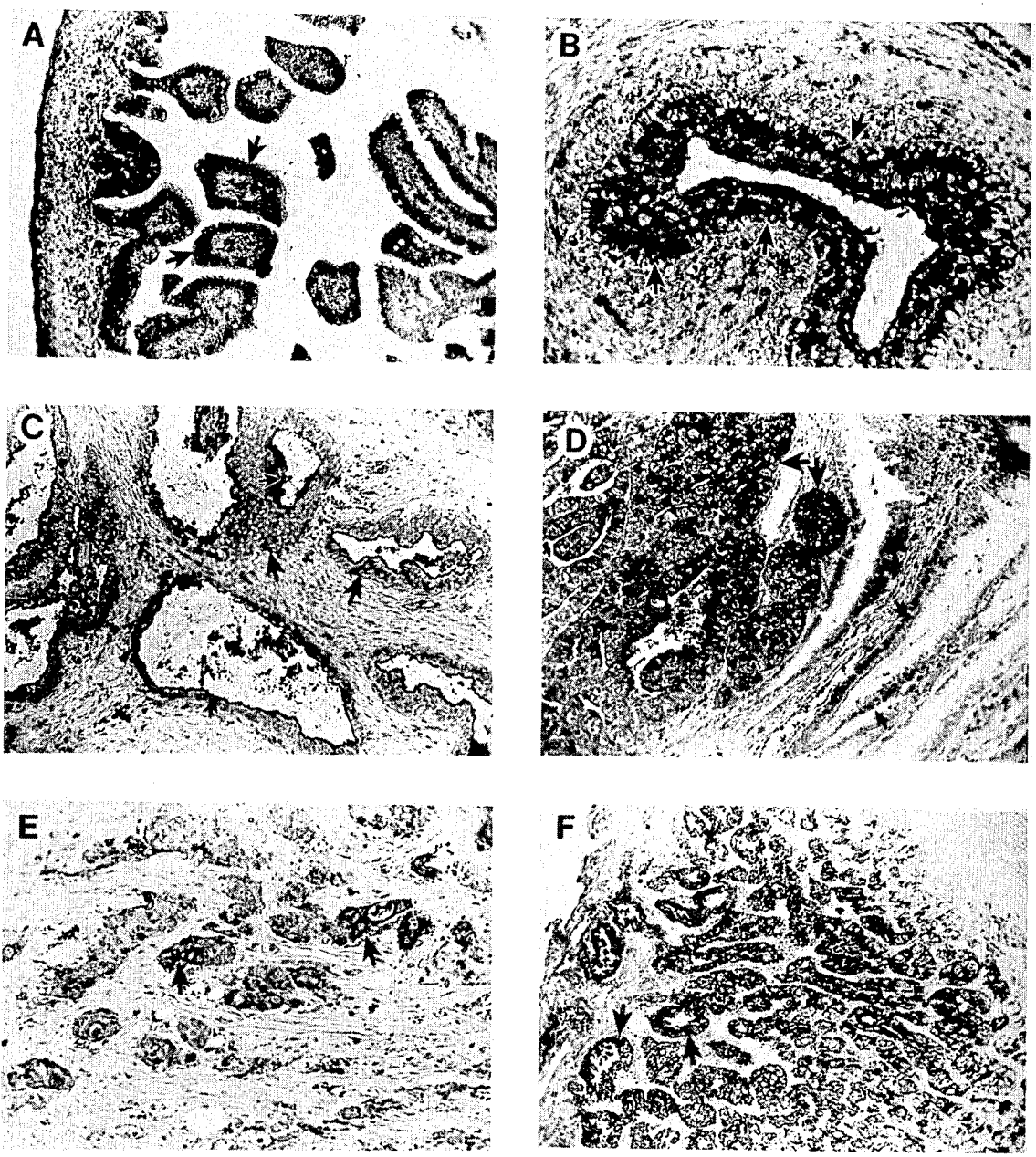
FIG. 4 shows six micrographs (A–F) demonstrating typical immunohistological staining of fetal and cancer tissues with the antibody FH6 coupled to a detectable marker, as described in Example 7; and, FIG. 5 is a chart as described in Example 8 showing the level of antigen reacting to the antibody FH6 in sera of patients with cancer (Ca) and normal subjects, wherein the types of cancer and the number of patients tested (in parentheses) are stated in the left ordinate, the level of reactivity is expressed on the absciscas, the positive ratios (% Positive) are shown on the right ordinate, and the following abbreviation apply: Gast., gastrointestinal; e.c., early case (stages I–II); Perit., peritoneal; Pancr., pancreatic; Oesoph., esophageal; Myoc. Infarct., myocardial infarction.

FIG. 4 shows typical immunohistological staining of fetal and cancer tissues with the antibody FH6. FIG. 4A is a paraffin section of small intestine of 72-day-old fetus. Note that strong staining was observed at the epithelial layer (arrows) facing the internal lumen. FIG. 4B is a paraffin section of colon of 54-day-old fetus. A strong positive staining occurred at epithelia (arrows) facing the internal lumen. FIG. 4C is a frozen section of adenocarcinoma of colon. Staining was found exclusively in the cancer cell mass (large arrow). A specific strong reaction was observed in the apical cytoplasm facing the internal lumen. FIG. 4D is a paraffin section of adenocarcinoma of stomach. A strong positive staining was observed in the cancer cell mass (large arrow), while cell and tissues of adjacent normal mucosa were negative (small arrow). FIG. 4E is a paraffin section of infiltrating ductal carcinoma of breast cancer. Only tumor cells (arrows) were positive, in contrast to adjacent normal tissues, which were negative. FIG. 4F is a paraffin section of well-differentiated renal adenocarcinoma. Cancer cells forming tubular structure (arrows) were strongly stained.

In tissues stained by the antibody FH6, the antigen distribution is characterized by a very dense positive region located at the apical surface of tumor cell layers facing the internal lumen of the adenocarcinoma. A typical example is shown in FIG. 4C. The antigen is expressed in differentiated adenocarcinoma but not in undifferentiated tumors, irrespective of their origins. Some stomach, colonic, lung, and breast cancers that were not stained by FH6 were less-differentiated cancers. A similar correlation between antigen expression and the degree of differentiation of tumor tissues was described previously for the expression of difucosyl type 2 chain antigen defined by FH4. *J.Exp.Med.* 159: 506–520, 1984.

Discussion

In a previous study, glycolipid antigens with di- or trifucosyl type 2 chain structure ($III^3V^3Fuc_2nLc_6$; $III^3V^3VII^3Fuc_3nLc_8$) were defined by monoclonal antibodies FH4 and FH5. *J.Biol.Chem.* 259: 4681–4685, 1984. Immunoperoxidase staining of a large variety of normal adult and fetal tissues as well as various human cancer tissues indicated that expression of those antigens is oncofetal; i.e., the antigens are expressed maximally at a certain stage of ontogenesis, regress greatly after organogenesis is completed, and are expressed in adult tissue only in certain types of cells such as parietal cells in gastric epithelia, Paneth's cells, and basal granular cells in the small intestine. In contrast, those glycolipid antigens with di- or trifucosyl type 2 chain structure are expressed strongly in various types of human adenocarcinomas such as gastric, colonic, and breast cancer.

The antigen defined by FH6 is indentified here as a sialyl-X (or sialyl-Le$^x$) carried by di- or trifucosyl type 2 chain as well as a long type 2 chain. However, the sialyl-X determinant carried by a short type 2 chain (nLc$_4$) did not react with the antibody FH6. This contrasts with the reactivity of a similar antibody, CSLEXI, which reacts with all sialyl-X determinants irrespective of their carrier structure. *Cancer Res.* 44: 5279–5285, 1984. Thus, the antigen distribution determined by immunohistology with the antibody FH6 must be quite distinctive from that defined by the CSLEXI antibody.

Another monoclonal antibody of interest is the antibody N-19-9. *Science* 212: 53–55, 1981; *J.Biol.Chem.* 257: 14365–14369, 1982. The antigen sialyl-Le$^a$ defined by the antibody N-19-9 has been in a large variety of tumors, particularly gastrointestinal tumors including pancreatic cancer (*Cancer Res.* 42: 4820–4823, 1982), and its distribution in normal tissue is restricted to specific loci such as ductal epithelia of pancreas, crypt area of stomach, and salivary glands (*Hybridoma* 2: 219–229, 1983). Recently, a high level of the antigen defined by antibody N-19-9 was found in seminal fluid. *Physiol.-Chem.* 365: 613–617, 1984.

TABLE 4 summarizes the results of various studies, including those described above, that compare the expression of the structurally related tumor-associated antigens sialyl-Le$^a$, sialyl Le$^x$, sialyl dimeric Le$^x$, and dimeric Le$^x$ in normal and tumor tissues and in sera.

TABLE 4

Comparative expression of structurally related tumor-associated antigens in normal and tumor tissues and in sera

| | Sialyl-Le[a] | Sialyl Le[x] | Sialyl dimeric Le[x] | Dimeric Le[x] |
|---|---|---|---|---|
| Expression in normal tissue | | | | |
| +++ | Seminal fluid[a] | Esophagus mucosa[b]<br>Proximal tubuli<br>Henle's loop | Proximal tubuli[c] | Proximal tubuli[d]<br>Henle's loop |
| ++/+ | Gallbladder epithelia[e]<br>Ductal epithelia of pancreas<br>Salivary glands<br>Endometrial mucosa<br>Goblet cells of colon | Deep crypt of colon[b]<br>Alveolar macrophage<br>Acinar cells of pancreas<br>Hepatic cells<br>Kupffer cells<br>Ureter and granulocytes | Granulocyte | Parietal cells[d] (stomach)<br>Pylorus mucosa (stomach)<br>Paneth's cells (intestine) |
| − | Stomach[e]<br>Intestine<br>Colon<br>Mammary glands<br>Kidney tubules and cortex epithelia<br>(Other tissues not reported) | Stomach[b]<br>Lung<br>Bronchia<br>Bile ducts<br>Pancreas<br>Brain<br>Thymus<br>Epidermis<br>Sweat glands<br>Arteries, veins<br>Ovary<br>Uterus<br>Adrenals<br>Nerves | Stomach[c]<br>Colon (even crypt area)<br>Liver<br>Small intestine<br>Mammary glands<br>Lung<br>Skin<br>Uterus<br>Brain | Colon[d] (even crypt area)<br>Esophagus<br>Pancreas<br>Liver<br>Gallbladder<br>Adrenals<br>Thymus<br>Skin<br>Heart<br>Muscle<br>Brain<br>Nerves<br>Arteries and veins |
| Expression in tumor tissue of | | | | |
| Colon | 59%[g] | 76%[b] | 33%[c] | 90%[d] |
| Pancreas | 86% | 100% | NR[h] | |
| Stomach | 89% | 94% | 60% | 75% |
| Liver | 9% | NR | NR | [95%][i] |
| Esophagus | NR | 50% | NR | |
| Lung | | | | |
| Adenocarcinoma | NR | 78% | 50% | 0% |
| Squamous | NR | 50% | NR | NR |
| Undifferentiated | NR | 33% | NR | NR |
| Breast | NR | 25% | 86% | 75% |
| Antigen level[j] in sera of patients with cancer of | | | | |
| Colon | 39%[b] | 35%[b] | 25%[c] | Not detectable in sera |
| Stomach | 43% | 19% | 33%(16%)[k] | |
| Breast | 18% | 52% | 14% | |
| Lung | 50% | 34% | 71% | |
| Pancreas | 85% | NR | 66% | |

[a]Physiol. Chem. 365:613–617, 1984.
[b]Cancer Res. 44:5279–5285, 1984.
[c]This study.
[d]J. Biol. Chem. 259:4681–4685, 1984.
[e]Hybridoma 2:219–229, 1983.
[f]Percentage of expression in tumor tissue denotes percentage of positive cases in immunohistology to the total number of cases examined.
[g]Cancer Res. 42:4820–4823, 1982.
[h]NR, not recorded.
[i]Unpublished data.
[j]Percentage of expression in antigen level in sera denotes percentage of positive cases of the total number of cases examined. The cases showing higher levels of antigen than normal are identified as "positive".
[k]Stage I cases in parenthesis.
[l]Ruibal, A., et al., In: Abstract Book (Abstract 80), Advances in Cancer Research, Proceedings of the XI Annual Meeting, Stockholm, Sweden, September 11 to 15, 1983.

The following characteristic features of the antigen expression and distribution defined by the antibody FH6 can be summarized: (a) The expression of the antigen defined by FH6 in human gastrointestinal cancer was weaker and less frequent than that of the antigens defined by FH4, CSLEXI, and N-19-9. On the other hand, the incidence of FH6 antigen expression in lung and breast cancer was obviously higher than that of FH4 antigen. (b) Essentially no staining by FH6 was observed in various adult tissues, including gastrointestinal and glandular epithelial tissues in which CSLEXI and N-19-9 showed positive staining. FH6-positive loci in normal adult tisue were limited to granulocytes and the proximal convoluted tubuli in kidney. In contrast, FH4 antigen was found in parietal cells, the pyloric area of gastric epithelia, basa granular cells, and Paneth's cells of the small intestine in addition to the proximal convoluted tubuli and thin limb of Henle's loop of the kidney. Normal granulocytes were very weakly stained with FH4 antibody in cytofluorometric analysis (*J.Immunol.* 134: 2498–2506, 1985). The sialyl-Le$^a$ defined by N-19-9 is abundantly present in normal seminal fluid, gallbladder epithelia, ductal epithelia of pancreas, and salivary glands. The sailyl-Le$^x$ defined by CSLEXI is present is esophagus mucosa, crypt of the colon, acinar cells of the pancreas, and hepatic cells, in addition to proximal tubuli, Henle's loop, and granulocytes. (c) In feta tissue, the FH6 antigen was widely expressed in various epithelial tissues thus far examined, although the intensity of staining was weak. Fetal tissues were diffusely stained by FH6 in the gastrointestinal and lung epithelia, in striking contrast to a specific focal localization of the FH4 antigen (*J.Biol.Chem.* 259: 4681–4685, 1984). Thus, the reactivity of the antibody FH6 is uniquely defined in accordance with the expression of the four structurally related tumor-associated antigens: sialyl-Le$^a$, sialyl-Le$^x$, dimeric Le$^x$, and sialyl dimeric Le$^x$.

EXAMPLE 8

Determination of levels of the antigen defined by antibody FH6 in serum of patients with cancer Plasma from 24 patients with various cancers was obtained from the Department of Medical Oncology, Veterans Administration Hospital, Seattle, WA. Sera from 117 patients with various cancers, 17 normal subjects, and 39 patients with acute and chronic inflammatory diseases were collected at Kyoto University School of Medicine. Plasma and sera of cancer patients were obtained from Stage III or IV, except for a group of earyl gastric cancers that were in Stage 1. The samples were immediately used for radioimmunoassay.

The antigen level in serum was determined by binding of $^{125}$I-labeled antibody FH6 on polystyrene plastic beads that were coated with the nonlabeled antibody FH6 and reacted with serum. The antibody FH6 was purified by gel filtration through Sephadex G-200 and labeled with [$^{125}$I]iodogen. Plastic beads were coated with the purified antibody FH6 as described in *J.Med.-Virol.* 2: 77–87, 1978. Serum samples (20 μl) were mixed with 200 μl of 50 mM citrate buffer (pH 4.5), and the mixture was incubated with the FH6-coated plastic beads for 18 hours at 25° C. with occasional rotation. The beads were washed three times with the buffer (pH 4.5, 50 mM citrate) and incubated with 200 μl of $^{125}$I-labeled FH6 antibody in 50 mM citrate buffer (pH. 4.5) for three hours at 25° C. with rotation. The radioactivity of $^{125}$I-FH6 given per one assay was approximately 100,000 cpm, and the radioactivity retained on the beads was counted after three washing of the beads with the same buffer solution.

The results showed that a significantly higher level of antigen was found in sera of patients with various cancers as compared with inflammatory diseases and with normal subjects. The antigen level in sera of normal subjects was less than 1.000 cpm. These results are summarized in FIG. 5. Those patients showing high antigen levels had advanced stages of cancer (Stages III and IV). One group of patients with Stage I or II gastric cancer showed a lower incidence of positive cases. Determination of the antigen level in plasma was disturbed by the presence of an unknown plasma component, nonspecifically reactive with FH6 antibody (data not shown).

Figure 5:
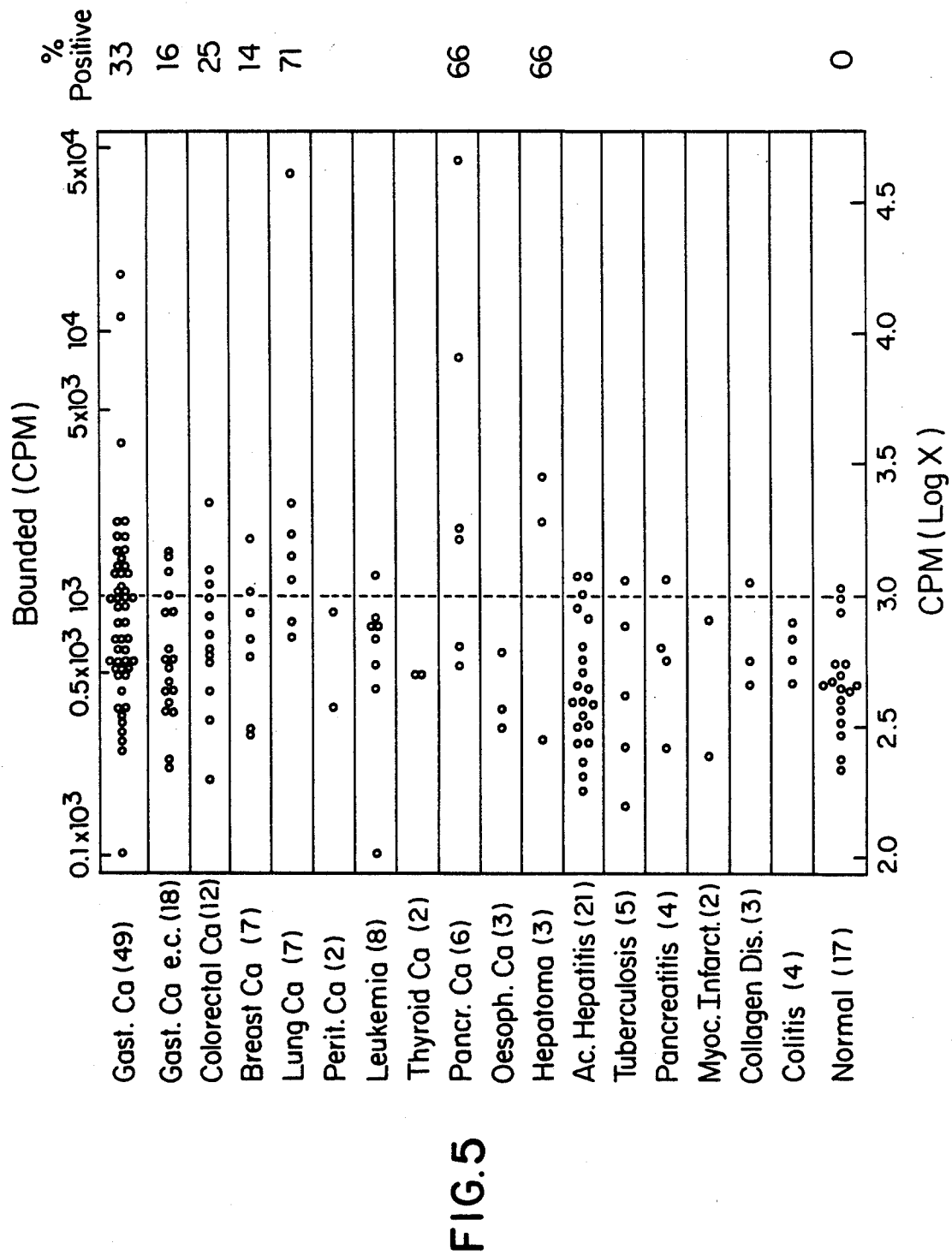

The level of FH6 antigen in sera of some patients with cancer was higher than that in the sera of patients with acute and chronic inflammatory diseases and normal subjects, although the antigen level in many cancer cases remained the same as the normal level. A higher incidence of high levels of serum antigen was found in lung, gastric, colorectal, liver, and pancreatic cancer. While the incidence of the antigen expression was very high in breast cancer tissue, the serum level in patients with breast cancer was relatively low. The detectable level of serum antigen can be correlated with a number of factors such as releasability of the antigen, location and stage of tumors, histological properties of tumors, etc. Thus, serum antigen levels may not simply reflect the degree of antigen expression in tumor tissues. The FH4 antigen, representing the asialo core of the FH6 antigen, was highly expressed in many gastrointestinal tumors, but the antigen levels in sera or plasma of the majority of patients with gastrointestinal tumors were the same as in normal subjects (data not shown). The level of G$_{D3}$ antigen was not found to be elevated in melanoma patients, although G$_{D3}$ is highly expressed in melanoma (data not shown). The serum level of artigen defined by the antibody FH6 was clearly high in some cases of cancer, although those cases showing high antigen levels were mostly Stages III and IV patients. One group of patients with early gastric cancers in Stage I showed 16% of positive antigen level. The incidence of high levels of antigen cannot be exactly compared with the data for N-19-9 and CSLEXI antibodies. Recent comparative analysis of sialyl-Le$^a$ and sialyl-Le$^x$ levels in Stage III and IV patients showed a similar rate of detection for gastrointestinal and lung cancer, but in some cases these two antigens were detected complementarily. *Cancer Res.* 45: 435–437, 1985. In the other hand, the detection rate of sialyl-Le$^a$ antigen by N-19-9 antibody in Stage I and II patients was very low (0% for Stage I, 16% for Stage II of gastric cancer. (Quentmeier, A., et al., Carbohydrate antigen 19-9 and carcinoembryonic antigen in gastric cancer detection, staging, and follow up. In: Abstract Book: Advances in Cancer Research (Abstract 21). Proceedings of the XI Annulal Meeting, Stockholm, Sweden. Sept. 11 to 15, 1983). This is similar to the present data for early gastric cancer cases, as shown in FIG. 5. Obviously, much technical improvement, e.g., by way of signal amplification, is needed to detect tumor-associated antigens, including antigen defined by the antibody FH6, in patient sera during the early stages of cancer.

The factors affecting immunologically detectable levels of serum antigens are unknown. The degree of shedding from tumors and the degree of immune complexes in serum can be taken into consideration. Although the incidence of high antigen levels in cancer patients was relatively low and only obvious at Stages III and IV as detected using FH6 by the present methods, the antibody FH6 may still be useful in diagnosing human cancer using serum samples, particularly if combined with antibodies for multiple tumor markers and if more sensitive methods are developed. On the other hand, antigen located in tumors but not shed into the blood should be a better target for the labeled antibody for diagnostic or therapeutic purposes because antigen shedding from tumors is the major cause of failure in targeting antibody probes or immunotoxins (*Science* 219: 644–650, 1983).

The antigen defined by the antibody FH6 is highly restricted to differentiated human cancer, and its restricted presence in normal tissue is well defined. For example, the antibody FH6 is highly specific for immunohistological detection of human colonic cancer (see FIG. 4C). Results from an extensive study using the FH6 antibody for immunohistological detection of human colon cancer indicate that the FH6-defined antigen is highly specific for both proximal and distal colon cancer. Thus, it is contemplated that radiolabeled antibody FH6 will also be particularly useful for imaging tumor location in vivo. For example, a radionuclide such as I-123 can be coupled to the antibody using standard methodologies, such as those employing the Bolton-Hunter reagent. The radiolabeled antibody can be admixed in a suitable carrier solution and introduced, e.g., intravenously or rectally, into the body of a mammal. The body can be thereafter scanned with scintillation detector means, such as a gamma camera, to localize tumor tissue bearing antigen reactive with the radiolabeled antibody FH6.

The antibody FH6 is also suitable for implementing cancer immunological therapy. The antibody FH6 can be coupled to a radionuclide or antitumor drug and introduced, such as by intravenous injection, into the body of a mammal in order to target and differentially deliver the radionuclide or drug to tumor tissues bearing antigen reactive with the FH6 antibody.

The antibody FH6 is also useful for detecting or delivering immunoregulatory or differentiation inducer agents to human granulocytes and human leukemic leucocytes, either in vivo or in vitro. For example, the antibody FH6 can be conjugated with interferon, retinoids (retinoic acids, retinol), butyric acid and other agents that may induce differentiation and provide functional diversity in the targeted cells. In this manner a highly malignant cancer cell can be converted to less malignant or even nonmalignant cells. Normal granulocytes can be similarly targeted and regulated for therapeutic effect by conjugating the antibody FH6 with, e.g., an immunosuppressive agent.

While the present invention has been described in conjunction with preferred embodiments, one of ordinary skill after reading the foregoing specification will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A hybridoma cell line having the characteristics of ATCC No. HB 8873, capable of producing a monoclonal antibody capable of specifically binding with the fucoganglioside $VI^3NeuAcV^3III^3Fuc_2nLc_6$ but not specifically binding with the fucoganglioside $IV^3$-$NeuAcIII^3FucnLc_4$.

2. The hybridoma cell line of claim 1, capable of producing a monoclonal antibody capable of specifically binding with fucogangliosides selected from the group consisting of $VI^3NeuAcV^3III^3Fuc_2nLc_6$ and $VI^3NeuAcV^3FucnLc_6$ but not specifically binding with $IV^3NeuAcIII^3FucnLc_4$, $IV^3NeuAcIII^4FucLc_4$, $VI^6$-$NeuAcIII^3FucnLc_6$, $V^3III^3Fuc_2nLc_6$, $IV^3NeuAcnLc_4$, or $VI^3NeuAcnLc_6$.

3. An IgM antibody produced by the hybridoma cell line of claim 1.

4. A monoclonal antibody produced by the hybridoma cell line of claim 1.

5. The monoclonal antibody of claim 4 coupled to a radionuclide.

6. The monoclonal antibody of claim 4 coupled to an antitumor drug, an immunoregulatory agent, or a differentiation inducer agent.

7. The monoclonal antibody of claim 4 coupled to a detectable marker.

8. The monoclonal antibody of claim 7 wherein the detectable marker is selected from the group consisting of enzymes, chromophores, fluorophores, coenzymes, chemiluminescent materials, enzyme inhibitors, and radionuclides.

9. A method of immunohistological detection of cells expressing the fucoganglioside $VI^3NeuAcV^3III^3$-$Fuc_2nLc_6$, comprising the steps of:
    (a) contacting the cells with the antibody of claim 7;
    (b) removing unreacted antibody from the cells; and
    (c) thereafter detecting the detectable marker coupled to reacted antibody on the cells.

10. The method of claim 7 wherein the cells are cancer cells.

11. The method of claim 10 wherein the cells are colonic cancer cells.

12. The method of claim 9 wherein the cells are granulocytes.

13. In a method of detecting tumor-associated antigen in blood serum including the steps of contacting the serum with antibody directed to tumor-associated antigen and detecting any reaction between the antibody and the antigen, the improvement comprising contacting the serum with the antibody of claim 4.

* * * * *

UNITED STATES PATENT AND TRADEMARK OFFICE
CERTIFICATE OF CORRECTION

PATENT NO. : 4,904,596

DATED : February 27, 1990

INVENTOR(S) : Hakomori et al.

It is certified that error appears in the above-identified patent and that said Letters Patent is hereby corrected as shown below:

On the title page, item [19] et al should be added.

Section [75], line 1: "Inventor:" should be --Inventors:--

Section [75], line 2: after "Wash." insert --; Edward D. Nudelman, Seattle, Wash.; Yasuo Fukushi, Sendai, Japan; and Reiji Kannagi, Kitaku, Japan.--

Section [56], first-listed publication under Other Publications: "pp. 3711-3777" should be --pp. 3711-3717--

Section [57] (Abstract), fourth line from last: "cels" should be --cells--

Column 1, line 60: "FHB≢" should be --FH6 --

Column 2, line 48: "abbreviation" should be --abbreviations--

Column 6, line 7: "by" should be --for--

Column 6, lines 54-55: after "1983." there should be no new paragraph division

Column 7, line 22: "structures" should be --structure--

Column 7, line 30: "NeAc" should be --NeuAc--

Column 7, line 46: "Costart" should be --Costar--

Column 8, line 12: "Reactive" should be --Reactivities--

Column 8, line 34: "4685" should be --4681--

Column 8, line 48: "a" should be --as--

Column 9, line 55: "decline" should be --declines--

Column 10, line 10: "quality" should be --quantity--

Column 10, line 33: "sample" should be --samples--

Column 12, line 6: "0.5M" should be --0.05 M--

Column 12, lines 11-12: "perioxidase" should be --peroxidase--

UNITED STATES PATENT AND TRADEMARK OFFICE
CERTIFICATE OF CORRECTION

Page 2 of 3

PATENT NO. : 4,904,596
DATED : February 27, 1990
INVENTOR(S) : Hakomori et al.

It is certified that error appears in the above-identified patent and that said Letters Patent is hereby corrected as shown below:

Columns 13-14, bottom of Table 2: insert

--[a] P, paraffin-embedded section; F, frozen section; ND, not done.

[b] +, positive; ±, weakly positive; -, negative.

[c] Numerator, case number with the indicated reactivity; denominator, number of cases examined.

[d] Smears fixed with acetone.--

Column 15, line 10: after "addition," insert --among--

Column 15, line 38: "parafin-embedded" should be --paraffin-embedded--

Column 15, line 64: "cell" should be --cells--

Column 16, line 53: after "been" insert --found--

Column 18, second subtitle in left column of Table 4: "Expression in tumor tissue of" should be --Expression[f] in tumor tissue of--

Column 18, bottom row of "Sialyl-Le$^a$" column, Table 4: "85%" should be --85%[1]--

Column 19, line 10: after "various" insert --normal--

Column 19, line 13: "tisue" should be --tissues--

Column 19, line 16: "basa" should be --basal--

Column 19, line 24: "sailyl-Le$^x$" should be --sialyl-Le$^x$--

Column 19, line 25: "is" should be --in--

Column 19, line 28: "feta" should be --fetal--

Column 19, line 51: "earyl" should be --early--

Column 20, line 2: "washing" should be --washings--

UNITED STATES PATENT AND TRADEMARK OFFICE
CERTIFICATE OF CORRECTION

PATENT NO. : 4,904,596

DATED : February 27, 1990

INVENTOR(S) : Hakomori et al.

It is certified that error appears in the above-identified patent and that said Letters Patent is hereby corrected as shown below:

Column 20, line 52: "In" should be --On--

Claim 10, line 1: "7" should be --9--

Signed and Sealed this

Fourth Day of June, 1991

Attest:

HARRY F. MANBECK, JR.

Attesting Officer

Commissioner of Patents and Trademarks